United States Patent [19]

Vogel et al.

[11] Patent Number: 4,829,549
[45] Date of Patent: May 9, 1989

[54] DENSITOMETER FOR SCANNING OS CALCIS FOR PREDICTING OSTEOPOROSIS

[76] Inventors: John M. Vogel, c/o University of California-Davis Medical Center, Sacramento, Calif. 95817; Philip J. Manly, c/o Osteon Incorporated, 649 California Ave., Wahiawa, Hi. 96786; Richard D. Wasnich, c/o Kuakini Medical Center, 347 N. Kaukini, Honolulu, Hi. 96817

[21] Appl. No.: 143,681

[22] Filed: Nov. 30, 1987

Related U.S. Application Data

[62] Division of Ser. No. 890,282, Jul. 29, 1986, abandoned, which is a division of Ser. No. 746,547, Jun. 19, 1985, abandoned.

[51] Int. Cl.$^4$ ............................................. G01N 23/00
[52] U.S. Cl. ......................................... 378/55; 378/54; 378/146; 378/208; 128/653; 128/659
[58] Field of Search ..................... 378/53–56, 378/186, 193, 196, 208; 128/133–134, 653, 659; 250/496.1, 506.1, 497.1, 498.1

[56] References Cited

U.S. PATENT DOCUMENTS 3,639,764  2/1972  Olson et al. ........................ 378/193
3,803,417  4/1974  Kok .................................... 378/196
4,260,898  4/1981  Annis .................................. 378/146

FOREIGN PATENT DOCUMENTS 8607531  12/1986  PCT Int'l Appl. .................. 378/53

Primary Examiner—Craig E. Church
Assistant Examiner—John C. Freeman
Attorney, Agent, or Firm—Nixon & Vanderhye

[57] ABSTRACT

The level of relative risk of osteoporosis in human subjects can be quickly determined by: measuring the bone mineral content of the os calcis (heel)—which is highly trabecular—and; assessing relative non-violent fracture risk at substantially all skeletal sites (both spinal and non-spinal) due to osteoporosis of the subject from the os calcis mineral content determination. The bone mineral content of a cortical bone site, such as the proximal radius (forearm), can also be determined. The densitometer apparatus includes a heel holding structure, or a forearm holding structure, which may be placed between a low energy source of gamma and/or x-rays, and a detector. The source and detector are mounted on a C-shaped yoke, which yoke can be moved horizontally and vertically during a rectilinear scan, and which can be rotated about a vertical axis when computed tomography (CT) capabilities are necessary.

4 Claims, 10 Drawing Sheets

```
PATIENT FILE # IS A93049
ROW   IO*    IO*SD  #IO*  #BAD   LIO*    MIO*    RIO*    BONE #1    BONE #2
1    918.3   45.7   129    0    943.4    0.0    901.3    65 -101    106-170
2    918.5   44.3   132    0    934.6   943.0   907.6    65  -98    108-168
3    922.7   48.7   141    0    925.6   990.0   914.9    66  -95    111-166
4    922.2   37.5   152    0    924.1   934.7   918.9    67  -92    115-163
5    934.6   43.4   158    0    931.6   923.9   938.7    67  -91    118-161
6    938.9   49.8   162    0    942.4   913.5   942.9    68  -89    119-159

STANDARD DATA FILE: SA15507
MG/SQCM SLOPE= 2.560948E-3    INTERCEPT= 6.600261E-3    STD I-O*= 736
GM/CM   SLOPE= 56.129478      INTERCEPT= -2.059811
```

|      | ULNA | | | | WIDTH | | CM | | RADIUS | | |
|------|------|------|------|------|-------|------|------|------|--------|------|------|
| ROW  | IO*  | CU   | MG/SQCM | GM/CM | ULNA | RADIUS | ULNA | RADIUS | CU | MG/SQCM | GM/CM |
| 1    | 918.3 | 22.8 | 237.52 | 0.442 | 37 | 65 |     |     | 47.2 | 281.13 | 0.878 |
| 2    | 918.5 | 21.4 | 242.78 | 0.417 | 34 | 61 |     |     | 44.7 | 283.64 | 0.833 |
| 3    | 922.7 | 23.3 | 300.50 | 0.452 | 30 | 56 |     |     | 47.4 | 327.88 | 0.881 |
| 4    | 922.2 | 26.5 | 395.55 | 0.509 | 26 | 49 |     |     | 49.2 | 389.75 | 0.914 |
| 5    | 934.6 | 29.2 | 453.94 | 0.557 | 25 | 44 |     |     | 52.3 | 461.75 | 0.969 |
| 6    | 938.9 | 29.7 | 480.51 | 0.566 | 24 | 41 |     |     | 53.9 | 510.48 | 0.996 |
| MEAN | 925.9 | 25.5 | 351.80 | 0.490 |    |    |     |     | 49.1 | 375.77 | 0.912 |
| 1 - 3 | 919.8 | 22.5 | 260.27 | 0.437 |   |    | 1.35 | 2.43 | 46.4 | 297.55 | 0.864 |
| 2 - 4 | 921.1 | 23.7 | 312.94 | 0.459 |   |    | 1.20 | 2.21 | 47.1 | 333.76 | 0.876 |
| 3 - 5 | 926.5 | 26.3 | 383.33 | 0.506 |   |    | 1.08 | 1.99 | 49.6 | 393.12 | 0.921 |
| 4 - 6 | 931.9 | 28.5 | 443.34 | 0.544 |   |    | 1.00 | 1.79 | 51.8 | 453.99 | 0.960 |
|      |       |      | CENTRAL 50% | | BONE MINERAL | | | | | | |
| 1 - 3 |      | 11.6 | 255.70 | 0.244 |   |    | 0.71 | 1.23 | 24.5 | 311.46 | 0.473 |
| 2 - 4 |      | 11.6 | 284.64 | 0.243 |   |    | 0.64 | 1.12 | 25.2 | 352.65 | 0.486 |
| 3 - 5 |      | 12.2 | 333.58 | 0.254 |   |    | 0.57 | 1.00 | 25.8 | 404.16 | 0.496 |
| 4 - 6 |      | 12.4 | 370.26 | 0.257 |   |    | 0.52 | 0.91 | 26.3 | 453.57 | 0.505 |

*Fig. 10*

| | A | | B | C | | D | |
|---|---|---|---|---|---|---|---|

PATIENT FILE # IS B93049

| ROW | IO* | IO*SD | #IO* | #BAD | LIO* | MIO* | RIO* | BONE #1 | BONE #2 |
|---|---|---|---|---|---|---|---|---|---|
| 1 | 912.4 | 67.0 | 171 | 4 | 966.4 | 832.0 | 909.0 | 58 - 82 | 114-140 |
| 2 | 911.3 | 69.7 | 175 | 0 | 963.9 | 829.5 | 906.7 | 58 - 82 | 114-140 |
| 3 | 892.9 | 52.9 | 170 | 3 | 918.8 | 830.5 | 896.6 | 56 - 81 | 113-140 |
| 4 | 889.7 | 47.2 | 171 | 6 | 922.0 | 830.2 | 890.4 | 57 - 81 | 115-139 |

STANDARD DATA FILE: SA1507
MG/SQCM SLOPE= 2.560948E-3    INTERCEPT= 6.600261E-3    STD I-0*= 736
GM/CM   SLOPE= 56.129478      INTERCEPT= -2.059811

ULNA                                                    RADIUS

| ROW | IO* | CU | MG/SQCM | GM/CM | WIDTH | | | CU | MG/SQCM | GM/CM |
|---|---|---|---|---|---|---|---|---|---|---|
| 1 | 912.4 | 47.5 | 738.93 | 0.882 | 25 | 33 | 27 | 51.3 | 738.99 | 0.950 |
| 2 | 911.3 | 47.7 | 742.85 | 0.887 | 25 | 33 | 27 | 50.8 | 732.57 | 0.942 |
| 3 | 892.9 | 47.8 | 715.38 | 0.888 | 26 | 33 | 28 | 51.4 | 713.54 | 0.952 |
| 4 | 889.7 | 47.1 | 733.05 | 0.876 | 25 | 35 | 25 | 47.6 | 740.26 | 0.884 |
| MEAN | 901.6 | 47.5 | 732.55 | 0.883 | | | | 50.3 | 731.34 | 0.932 |

ULNA  RADIUS
                                         CM

| 1 - 3 | 905.5 | 47.7 | 732.39 | 0.886 | 1.01 | 1.09 | 51.2 | 728.37 | 0.948 |
| 2 - 4 | 898.0 | 47.5 | 730.43 | 0.884 | 1.01 | 1.07 | 49.9 | 728.79 | 0.926 |

CENTRAL 50% BONE MINERAL

| 1 - 3 | | 28.9 | 844.31 | 0.552 | 0.53 | 0.56 | 31.8 | 884.98 | 0.604 |
| 2 - 4 | | 28.9 | 844.77 | 0.552 | 0.53 | 0.55 | 30.6 | 872.45 | 0.583 |

| ROW | ECH | ECH | LEAN SIDE |
|-----|-----|-----|-----------|
| 1   | 93  | 162 | A |
| 2   | 92  | 169 | A |
| 3   | 92  | 175 | A |
| 4   | 89  | 178 | A |
| 5   | 86  | 178 | A |
| 6   | 82  | 171 | F |
| 7   | 78  | 166 | F |
| 8   | 72  | 164 | F |
| 9   | 66  | 162 | F |
| 10  | 62  | 162 | F |
| 11  | 57  | 161 | F |
| 12  | 53  | 160 | F |

SUBJECT FILE NAME  H93049
STANDARD DATA------  SA1507
MG SQCM------ SLOPE = 0.002561   INTERCEPT = 0.0066600
GM/CM------- SLOPE = 56.129478   INTERCEPT = -2.059811
WATER I-0 = 736

I-ZERO DATA

| ROW | HIGH | LOW | MEAN | CN | FAT EQU | LOW:H2O |
|-----|------|-----|------|----|---------|---------|
| 1   | 952.88  | 786.63 | 869.75 | 70  | 1.23 | 1.07 |
| 2   | 965.50  | 787.88 | 876.69 | 78  | 1.31 | 1.07 |
| 3   | 879.00  | 774.00 | 826.50 | 84  | 0.82 | 1.05 |
| 4   | 906.63  | 742.75 | 824.69 | 90  | 1.28 | 1.01 |
| 5   | 871.88  | 786.75 | 829.31 | 93  | 0.66 | 1.07 |
| 6   | 978.63  | 819.25 | 898.94 | 90  | 1.14 | 1.11 |
| 7   | 1042.50 | 793.13 | 917.81 | 89  | 1.76 | 1.08 |
| 8   | 1040.63 | 811.63 | 926.13 | 93  | 1.60 | 1.10 |
| 9   | 1109.25 | 822.75 | 966.00 | 97  | 1.92 | 1.12 |
| 10  | 1129.38 | 821.63 | 975.50 | 101 | 2.05 | 1.12 |
| 11  | 1118.50 | 834.75 | 976.63 | 105 | 1.88 | 1.13 |
| 12  | 962.75  | 826.00 | 894.38 | 108 | 0.98 | 1.12 |
| MEAN | 996.46 | 800.59 | 898.53 | 91  | 1.39 | 1.09 |
| SUM  |        |        |        | 1098 |      |      |

| ROW | LOW IO | | BONE DATA | | | MEAN IO | |
|---|---|---|---|---|---|---|---|
| | CU | MG/SQCM | GM/CM | H2O IO | | CU | MG/SQCM |
| | | | | CU | MG/SQCM | | |
| 1 | 102.36 | 568.44 | 1.860 | 97.71 | 542.46 | 109.40 | 607.66 |
| 2 | 83.56 | 415.76 | 1.525 | 78.25 | 389.16 | 91.90 | 457.47 |
| 3 | 78.45 | 362.09 | 1.434 | 74.22 | 342.43 | 83.96 | 387.72 |
| 4 | 79.07 | 340.47 | 1.445 | 78.25 | 336.91 | 88.49 | 381.33 |
| 5 | 83.98 | 350.01 | 1.533 | 77.77 | 323.97 | 88.88 | 370.58 |
| 6 | 89.43 | 385.43 | 1.630 | 79.79 | 343.59 | 97.78 | 421.68 |
| 7 | 88.33 | 384.96 | 1.610 | 81.68 | 355.77 | 101.32 | 441.98 |
| 8 | 97.58 | 407.13 | 1.775 | 88.48 | 368.94 | 109.85 | 458.66 |
| 9 | 102.52 | 410.12 | 1.863 | 91.71 | 366.61 | 118.09 | 472.80 |
| 10 | 100.79 | 387.08 | 1.832 | 89.67 | 344.10 | 118.13 | 454.11 |
| 11 | 105.14 | 388.44 | 1.910 | 91.93 | 339.28 | 121.63 | 449.74 |
| 12 | 126.15 | 453.54 | 2.284 | 113.69 | 408.49 | 134.74 | 484.60 |
| SUM | 1137.36 | 4853.47 | 20.704 | 1043.15 | 4461.73 | 1264.16 | 5388.32 |
| MEAN | 94.78 | 404.46 | 1.725 | 86.93 | 371.81 | 105.35 | 449.03 |

| ROW | LOW IO | | | AREA | BMC | BMD |
|---|---|---|---|---|---|---|
| | CU | MG/SQCM WEDGE | GM/CM | SQCM | GRAMS | GM/SQCM |
| 1 - 9 | 805.28 | 402.71 | 1.631 | 9.408 | 4.403 | 0.468 |
| 2 - 10 | 803.70 | 382.56 | 1.628 | 9.780 | 4.395 | 0.449 |
| 3 - 11 | 825.28 | 379.53 | 1.670 | 10.104 | 4.510 | 0.446 |
| 4 - 12 | 872.99 | 389.69 | 1.765 | 10.392 | 4.765 | 0.459 |

Fig. 13

DENSITOMETER FOR SCANNING OS CALCIS FOR PREDICTING OSTEOPOROSIS

This is a division of application Ser. No. 890,282, filed July 29, 1986, which in turn is a division of application Ser. No. 746,547, filed June 19, 1985, both of which are now abandoned.

Osteoporosis has been increasingly recognized as a prevalent debilitating condition. However when osteopenia is discovered at early stages, a variety of treatments can be prescribed which can effectively prevent progress to clinically significant osteoporosis. Exercise (particularly by weight loading bones), calcium supplements, estrogen, and estrogen thiazide combinations, can each be effective at different stages in progression. Even when there has been significant progression to clinically significant osteoporosis, some treatment strategies are available, including the administering of sodium fluoride. In view of the available treatment strategies, it has been widely recognized that techniques for the accurate, safe, and relatively inexpensive determination of the level of risk for osteoporosis are highly desirable.

Indiscriminant treatment of all postmenopausal women (who have by far by the highest propensity to osteoporosis in the population, irrespective of actual risk) is not cost-effective and is limited by low patient compliance. Bone mineral content (BMC), which has been demonstrated to correlate with skeletal strength, can be precisely measured by a variety of techniques, and at many different skeletal sites, however no prospective data has been available relating BMC to fracture incidence. Conventional understanding suggests that the prediction of fracture risk at a given site, such as the spine, necessarily requires direct BMC measurements of that site, and since it is not feasible to measure all potential fracture sites, and since it is not known ahead of time for any given individual which skeletal site might be at greatest risk, prediction of fracture risks by prefracture BMC measurements has not been implemented.

According to the present invention, an accurate, safe, and relatively inexpensive method has been developed for determining the level of risk for osteoporosis in humans. According to the present invention it has been surprisingly found that it is possible to predict fracture risk at multiple skeletal sites (substantially all skeletal sites), both spinal and non-spinal (including the hip) by screening individuals utilizing a single BMC measurement site. The word "fracture" as used herein means non-violent fractures incident to the osteoporotic syndrome.

It has been determined, after long term studies of a representative population of women of advanced age, that BMC measurement of the os calcis (heel) provides an effective predictor of both nonspine and spine fracture risk. In fact it has been found that subjects in the lowest quintile of os calcis BMC have a ten-fold increase of fracture risk, relative to subjects in the highest quintile. While the os calcis, a largely trabecular bone (trabecular bones being the most affected by the normal aging effects of osteoporosis) was one of the first bones used to estimate mineral content of the skeleton, before the invention the ability of BMC measurements of the os calcis to predict relative fracture risk at substantially all skeletal sites was unknown, and in fact it previously was suggested that there was no correlation of the radiographic trabecular patterns of the os calcis to the degree of osteoporosis.

Building upon the recognition of the suitability of os calcis BMC measurements to predict subsequent fracture incidence at substantially all skeletal sites, according to the present invention methods and procedures have been developed for facilitating the determination of the level of relative risk for osteoporosis, and for facilitating the prevention of osteoporosis. Widespread implementation of the procedures according to the invention can make clinically significant osteoporosis an anomaly among the present generation of perimenopausal women, as well as significantly reducing the incidence of hip fracture among postmenopausal women.

In one particular procedure according to the invention, a method of treating a human subject to minimize the risk of osteoporosis is practiced comprising the following steps: (a) At approximately the human subject's peak bone mass condition (e.g. at approximately age 35 for women), at least one of the human subject's trabecular bone sites is rectilinearly scanned (utilizing a low energy gamma and/or x-ray source) to develop an osteoporosis risk assessment. This is preferably accomplished by scanning a single bone, the os calcis. (b) After step (a), periodically scanning the at least one bone site (e.g. the os calcis) and comparing the scanning results with those in step (a) to assess increasing or decreasing osteoporosis risk.

Where a prescribed treatment for osteoporosis is a more aggressive type of treatment which will build trabecular bone at the expense of cortical bone (such as sodium fluoride treatments), it is also prudent to determine cortical bone density for the subject in order to properly monitor the treatment to minimize undesirable complications. According to the present invention it has been found that BMC measurements of the proximal radius (forearm) can be used to accurately predict the effects at all cortical skeletal sites. Since the distal radius is trabecular, BMC measurements of both the distal and proximal ends of the forearm can be utilized in the monitoring of preventative treatments.

According to another aspect of the present invention, a method of facilitating the prevention of osteoporosis in a human subject is provided. The method comprises the steps of: (a) determining the mineral content of a single trabecular bone of the human subject; and (b) predicting fracture risk at substantially all skeletal sites based upon the single trabecular bone mineral content determined in step (a). The single trabecular bone is preferably the os calcis, and it also may be prudent to practice the step of determining the mineral content of a single cortical site, preferably the proximal radius.

The invention also contemplates a simple method of screening human subjects (e.g. perimenopausal women) to quickly determine the level of risk for osteoporosis by simply (a) determining the bone mineral content of the os calcis of a human subject, and (b) assessing relative fracture risk at multiple (substantially all) skeletal sites of the human subject from the os calcis mineral content determined in step (a).

According to the present invention apparatus, generally known as a densitometer, has also been developed which greatly facilitates the practice of the methods according to the invention. The apparatus according to the invention allows the goal of accurate, safe, and relatively inexpensive determination of the level of risk of osteoporosis in perimenopausal women to become a reality. In addition, the apparatus according to the invention can be utilized to measure the response to treatment in individuals with established osteoporosis, and to monitor the effectiveness of preventative regimens. Utilizing the apparatus according to the invention it is possible to quickly and effectively determine the bone mineral content of the os calcis, and also preferably the proximal radius, and more preferably both the proximal radius and distal radius.

The bone scanning apparatus according to the present invention has a housing with means defining an opening in a top portion of the housing. A means for holding a body part of a human subject in proper position during scanning is disposed in the opening. Preferably the opening receives one of two different body part holding means, a heel holding structure for properly positio the os calcis during scanning, and a forearm holding tube for properly positioning both the proximal radius and distal radius.

The bone scanning apparatus also comprises a source of low energy radiation, specifically gamma rays and/or x-rays, such as iodine-125. A conventional detecting means is mounted opposite the source by a yoke which is disposed within the housing. The yoke has a C-shape in plan view, and includes a pair of opposed generally horizontally extending arms, one arm mounting the source and the other the detecting means. The volume between the arms is sufficient to receive the body part holding means therein. Means are provided for moving the yoke verically with respect to the holding means, and for moving the yoke horizontally with respect to the holding means. Also means are provided for rotating the yoke about a vertical axis with respect to the holding means where computed tomography (CT) capabilities are desired. In this way the yoke can be properly positioned for scanning either the os calcis or the radius, and for effecting the appropriate scans for each.

The yoke assembly according to the invention includes shutter means associated with the arm for holding the source, the shutter means ensuring that the source is shielded until the beam is required in the scanning process. The shutter means preferably comprises a shutter element rotatably mounted by a shaft and a bearing (which bearing is received by the yoke arm) for rotational movement with respect to the yoke arm. A sprocket is also mounted on the shaft and is connected by a belt to a solenoid and a spring. When the solenoid is actuated the sprocket is rotated, which in turn rotates the shaft and the shutter to unshield the source so that the beam is directed toward the detector. When operation of the solenoid is terminated, the spring automatically returns the shutter to its shielding position.

The holding means for holding the body parts according to the present invention are particularly adapted for holding the heel and the forearm. The heel holding apparatus positions the heel so that the os calcis is readily accessed by the scanning beam. The forearm holder holds the subject's arm so that both the distal radius and proximal radius are readily accessible to the scanning beam. In both cases, the holders are water tight, and water is utilized to fill the holders at least up to the top of the bone sites being scanned, to eliminate the effect of varying amounts of soft tissue covering the bone.

It is the primary object of the present invention to provide a method and apparatus for facilitating risk assessment of osteoporosis. This and other objects of the invention will become clear from an inspection of the detailed description of the invention, and from the appended claims.

BRIEF DESCRIPTION OF THE DRAWINGS

FIGS. 12a and 12b provide an example of a detailed report for the scanning of the os calcis.

DETAILED DESCRIPTION

It has been found that the os calcis and proximal radius bone mineral contents (BMC) have the most significant relationship to non-spine fracture prevalence. It has also been found that the os calcis BMC has the most consistent, monotonic relationship to non-spine fracture prevalence. The os calcis BMC also has the most consistent, monotonic relationship to spine fracture prevalence. In fact it has been found that subjects in the lowest quintile of os calcis MBC have a risk for future non-spine fractures which is ten times higher than subjects in the highest quintile. Thus, by routine risk evaluation of the os calcis, the level of risk for osteoporosis in an individual can be accurately, safely, and inexpensively assessed.

Since some treatment regimens for preventing progression to osteoporosis can have an adverse effect on cortical bone, according to the invention it is desirable to be able to determine the BMC of a highly cortical bone, as well as the os calcis (which is highly trabecular), in monitoring the effectiveness of treatment of the human subject. The proximal radius is primarily cortical bone, and has been found to be an excellent bone site for evaluation of changes in cortical bone. The distal radius in a mixture of cortical and trabecular bone, and in some risk evaluation and treatment procedures it is desirable to also be able to determine the BMC of the distal radius.

According to the present invention, an apparatus is provided for scanning of a human subject's bones. The apparatus is primarily used in the simple yet accurate screening of perimenopausal women to evaluate the risk of osteoporosis. However the apparatus also is useful in measuring the response to treatment in individuals with established osteoporosis, and in the monitoring of the effectiveness of preventive regimens.

Figure 1:
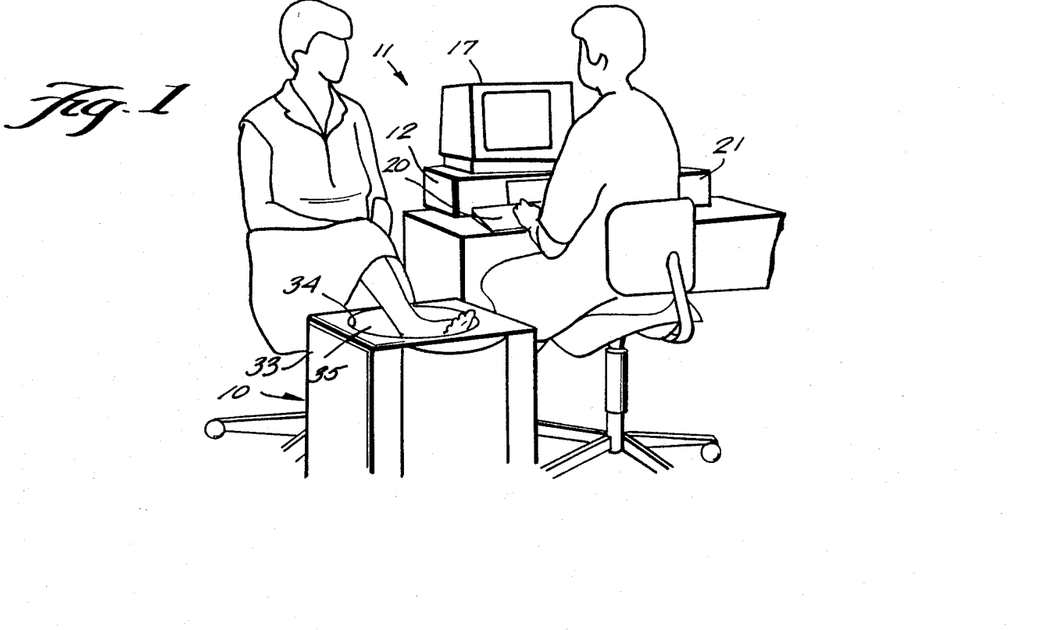
FIG. 1 is a perspective view of exemplary apparatus according to the present invention in use for scanning a female patient's os calcis.
Figure 2:
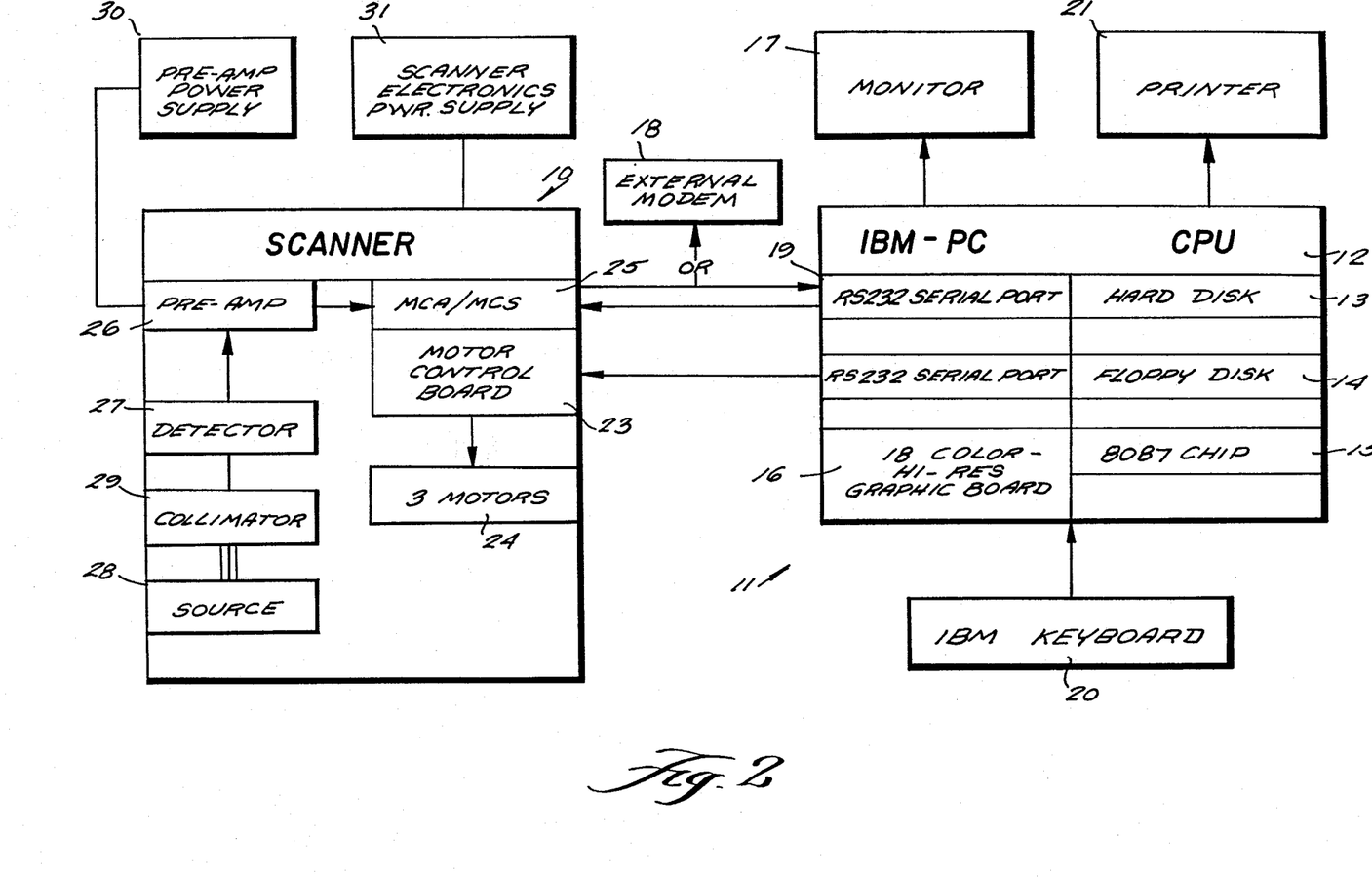
FIG. 2 is a block diagram showing the interconnection between various operational component parts of the apparatus of FIG. 1.

The bone scanning apparatus according to the present invention is illustrated schematically in FIGS. 1 and 2. Main components thereof include the actual scanning apparatus, shown generally by reference numeral 10, and a control system, shown generally by reference numeral 11, for controlling the scanning mechanism 10.

Various operational components of an exemplary apparatus are illustrated schematically in FIG. 2 with components that are housed together contained within the same box.

The control component 11 preferably comprises a computer, such as an IBM Personal Computer Central Processing unit 12. The computer controls the scanner, analyzer, and printer, and analyzes the data obtained. The hard disk drive 13 holds the data files, and program files, and stores pertinent data files. The floppy disk drive 14 holds data files, program files, and stores archival data files (back-up). Further it loads additional programs from the floppy disk drive to the hard disk drive. The 8087 chip 15 speeds up mathematical computations. The high resolution color graphics board 16 interfaces the computer 12 with the monitor 17 to provide high resolution graphics display. The computer communicates with the external modem 18 via the RS-232 serial port 19. The modem 18 itself provides access to updated research data bases and the like. The keyboard 20 is used to input commands to the computer 12, and includes a number of special function buttoms which initiate software controlled commands for operation of the scanner 10. The printer 21 provides a paper copy of the data/patient report.

Control components for the scanner 10 include the motor controller card 23 which controls three stepper motors, seen collectively as element 24 in FIG. 2, and their respective motor drivers. The multi-channel analyzer/scaler 25 collects data, separating counts from the source into channels. The pre-amplifier 26 provides the first step in amplifying very small signal outputs from the radiation detector 27, which is a conventional detecting means for detecting low energy gamma rays and/or x-rays. The source 28 is a source of low energy gamma rays and/or x-rays, such as an iodine-125 source, with an energy level of approximately 28 keV, useful activity of about 500–200 mCi, and a beam size of 3.2 mm at the detector (collimated). The collimator 29 collimates the rays from the source 28 prior to impact upon the detector 27. The pre-amp power supply 30 provides power to the pre-amplifier, and the scanner electronics power supply 31 supplies power to the scanner, MCA/MCS, and detector.

The CPU 12 initiates most communications. For example it initiates communications with the monotir 17 to display theoutput and request input from the operator. It initiates communication with the motor control board 23 controlling the duration and direction and initiation of operation of each of the three motors 24. It initiates communications with the MCA/MCS telling it how to scan, how long to scan, and when to scan; and it communicates with the external modem 18 via the serial port 19. Additionally the CPU 12 receives communications from other components. For instance it receives from the MCA data from the scanner. It receives from the motor control board 23 command verification and status of the motor positions.

Bone mineral content can be determined utilizing the source 28, detector 27, etc. since bone is an organic matrix incorporating a mineral component of hydroxyapatite, which has the property of attenuating low energy gamma rays or x-rays according to the exponential attentuation law $$I = I^*_o e^{-ux},$$

where:
 $I^*_o$ = original flux;
 $u$ = linear attenuation coeff;
 $x$ = thickness of material;
 $I$ = attenuated flux.

The bone mineral content can be related to the amount of attenuation of low energy gamma or x-ray beams. However, first it is desirable to determine the unattenuated flux of radiation by measuring the radiation count of a water box without anything else present. Then a bone site is placed in the water box and scanned. The water eliminates the effects of varying amounts of soft tissue covering the bone. The radiation beam will be attenuated where there is bone present in the water box. The amount of bone is determined by the log ratio of the attenuated to unattenuated flux when summed over the width of the bone. By calibration with a known standard, this log ratio sum can be related to the bone mineral content.

The mechanical components of the scanner 10 are most clearly seen in FIGS. 3 through 9. For clarity of illustration the housing 33 (see FIGURE 1) which encloses the scanner components is not illustrated in these other FIGURES. The housing 33 includes an opening 34 formed in the top thereof in which a means for holding a body part to be scanned is placed. Such a means is shown generally by reference numeral 35 in FIG. 1, for the particular structure of FIG. 1 comprising a heel holder for —as illustrated in FIG. 1—holding the heel of a human subject so that the os calcis can be scanned.

Figure 3:
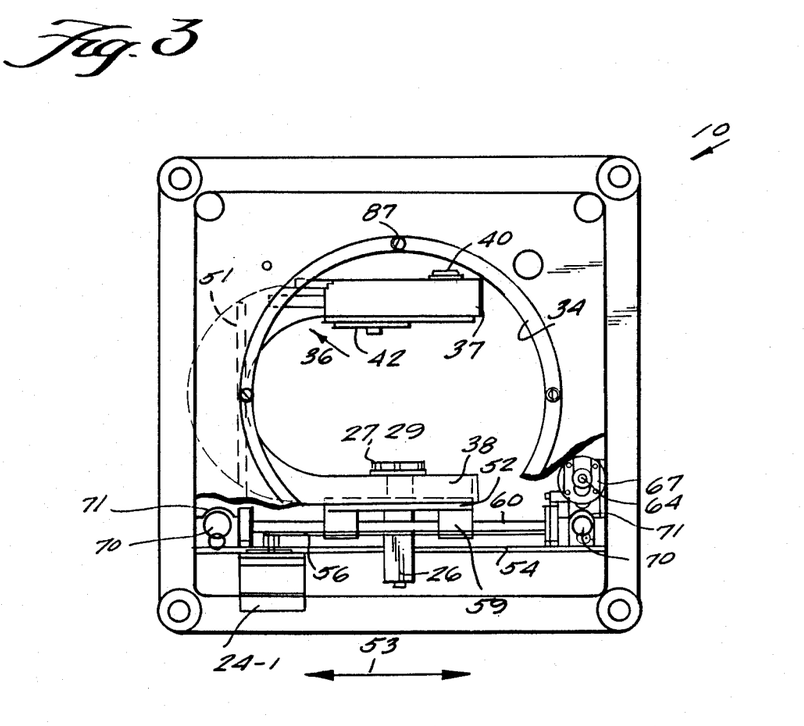
FIG. 3 is a top plan view, with portions cut away for clarity, of the mechanical scanning apparatus of FIG. 1.
Figure 4:
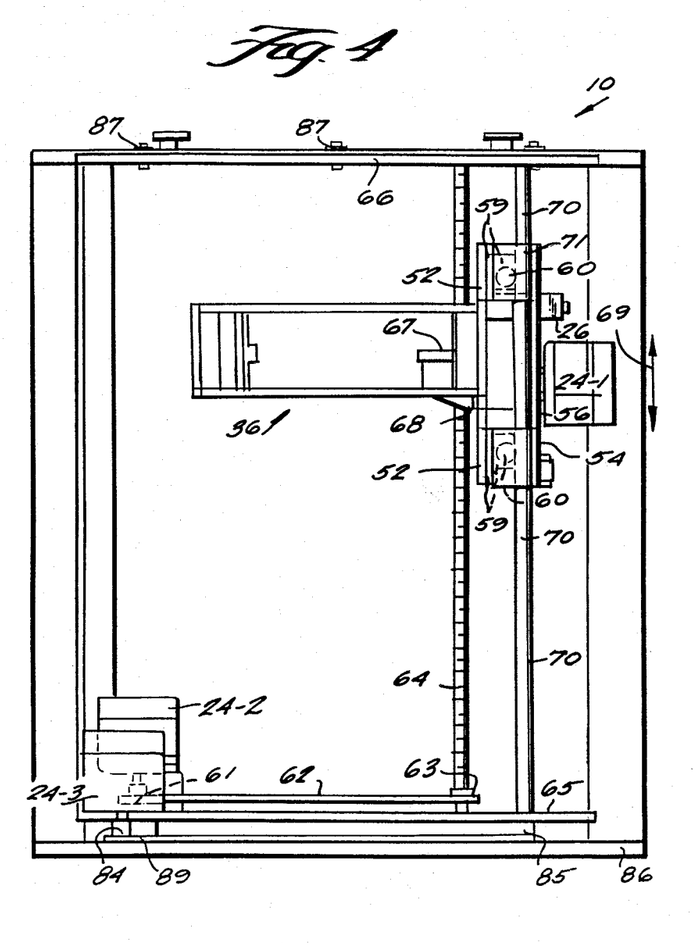
FIGS. 4 and 5 are side and end views, respectively, of the apparatus of FIG. 3 with the housing components removed for clarity of illustration.
Figure 6:
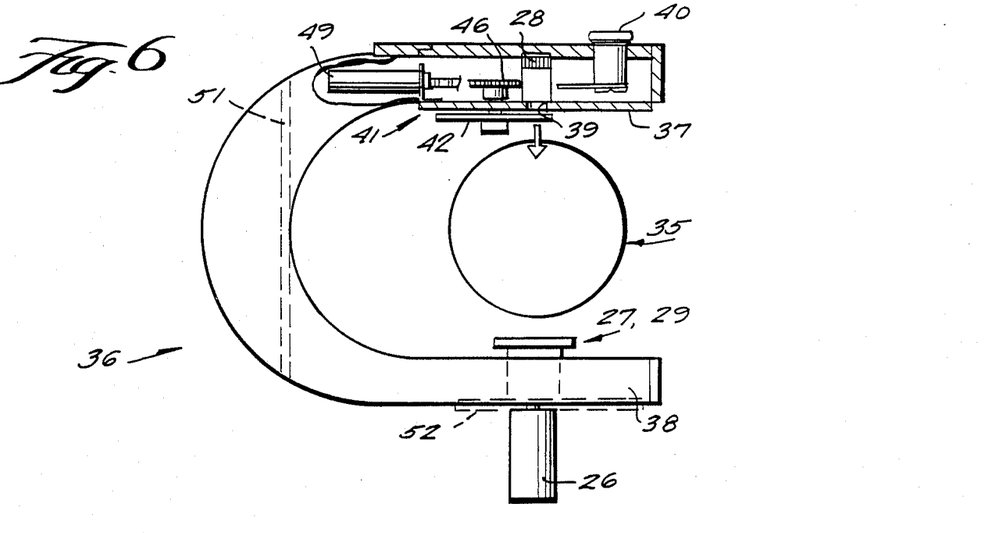
FIG. 6 is a top plan detail view, with portions cut away for clarity, of an exemplary yoke assembly according to the present invention.

A first important component of the scanning apparatus 10 is a yoke assembly, shown generally by reference numeral 36 in FIGS. 3, 4, and 6. The yoke assembly 36 preferably has a C-shape in plan view (FIGS. 3 and 6), and includes a first arm 37 and a second arm 38. The first arm 37, as seen in FIG. 6, mounts the radiation source 28. As illustrated in FIG. 6, the source 28 preferably is completely enclosed within the first arm 37 except for a small aperture 39 formed in a side wall of the arm 37 through which a radiation beam may pass, as indicated by the arrow in FIG. 6. The source 28 preferably, as schematically illustrated in FIGURE 6, is mounted in a brass cylindrical container which completely absorbs the low energy gamma and x-rays emitted by the iodine 125 held therewithin, except that which passes through the open end of the cylindrical container out the opening 39. A brass cap (not shown) is provided for the source 28 cylindrical container, and the brass cap can be threaded onto the open end of the container when it is removed from the arm 37 so that it may be safely handled and all radiation coming from the iodine 125 therewithin will be absorbed.

In order to allow only authorized entry to the interior of the arm 37 containing the source 28, a key operated locking means 40 (see FIG. 6) is provided. Only by opening the lock 40 with a key can access to the interior of arm 37 be gained, and thus removal of the source 28 be provided.

Figure 7:
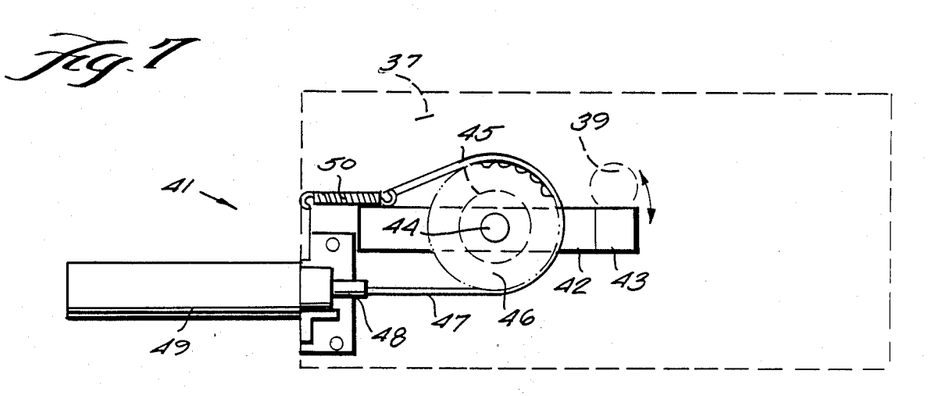
FIG. 7 is a top plan view of the shutter assembly utilized with the yoke assembly of FIGURE 6.

A collimator (not shown) also may be provided mounted directly at the open end of the source 28. In addition, shutter means, shown generally by reference numeral 41 in FIGS. 6 and 7, are provided for selectively allowing or preventing passage of radiation from the source 28 toward the detector 27.

The shutter means 41 preferably comprises a shutter element 42 including a lead section 43 thereof which is adapted to cover the opening 39 in arm 37. The shutter element 42 (see FIG. 6) is mounted on the external surface of the inner side of arm 37 by a central shaft 44, and preferably a thrust washer (not shown) is provided between the element 42 and the arm 37, the thrust water surrounding the shaft 44. The shaft 44 extends through a bearing 45 which is mounted in the side wall of the arm 37, and continues into the interior of the arm 37 with a sprocket gear 46 connected to the end of the shaft 44 within the interior of arm 37.

A drive belt 47 extends around a portion of the circumference of the sprocket gear 46 in operative association therewith. The drive belt 47 may comprise any suitable conventional drive belt, such as commercially available belts formed by two stainless steel wires with nylon teeth extending therebetween at precisely spaced locations. A first end of the drive belt 47 is connected to the linearly movable plunger 48 of a linear actuator, such as solenoid 49. The other end of the drive belt 47 is connected to a spring, such as coil tension spring 50. When the scanning of a particular row is initiated, coincident with stepper controller operation to perform that scanning operation the solenoid 49 is actuated so that the plunger 48 is withdrawn (as illustrated in FIG. 7) so that the belt 47 rotates the gear, and thus the shaft 44 and shutter element 42 connected thereto, so that the lead portion 43 of the shutter element 42 moves away from the opening 39 and thus a beam of radiation can pass from the source 28 to the detector 27. When scanning of that particular row is completed, solenoid 49 is deactivated, and the spring 50 thereupon automatically rotates the sprocket 46, and thus the shaft 44 and element 42, so that the lead portion 43 of element 42 goes over the opening 39 and prevents passage of radiation outside of the arm 37.

In the second arm 38 of the yoke assembly 36, the detector 27 and collimator 29 are mounted (see FIG. 6 in particular). Additionally pre-amplifier 26 may also be operatively mounted to the arm 38. Note that the detector 27 is mounted in alignment with and directly opposite the source 28 and so that there is an open volume therebetween, in which volume the heel holder 35, or like body part holding device, is adapted to be disposed.

The cross portion of the yoke 36 preferably includes a strengthening plate 51. Connected to the second arm 38 is a mounting plate 52 which is adapted to mount the entire yoke assembly 36 on means for moving the yoke assembly.

Figure 5:
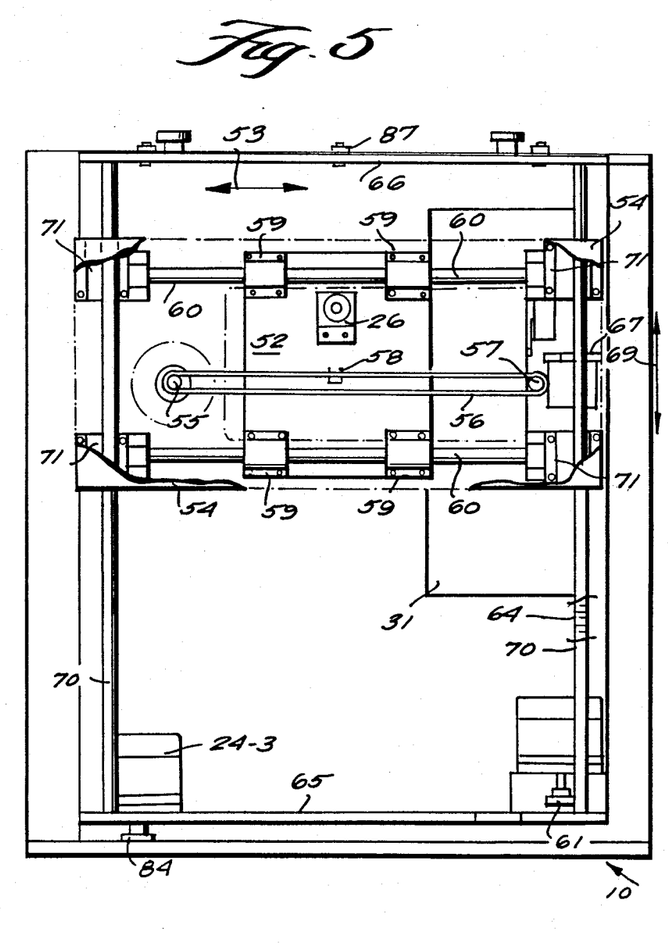

Another important feature of the scanning apparatus 10 is a means for moving the yoke assembly 36 horizontally, in the dimension indicated by arrows 53 in FIGS. 3 and 5, during the performance of a rectilinear scan. While the horizontal moving means may comprise a wide variety of structures, one exemplary particular such structure is illustrated in FIGS. 3 through 5.

The horizontal moving structure includes the first stepper motor, 24-1, which is mounted to plate 54, with the drive shaft for the motor 24-1 extending through the plate and terminating in drive sprocket 55 (see FIG. 5). An endless drive belt 56 (like the belt drive 47 only endless) wraps around the drive sprocket 55 and an idler sprocket 57. The mounting plate 52 for the yoke assembly 36 is clamped onto the drive belt 56, as with a conventional compression clamp 58 (see FIG. 5). Thus rotation of the drive sprocket 55 is transformed into a precisely known linear movement of the yoke assembly 36 in the dimension of arrows 53.

In order to mount the yoke assembly 36 for linear movement in dimension 53, a plurality of mounting brackets 59 are provided, which brackets 59 are rigidly connected to the plate 52 and have a C-shaped configuration, surrounding the guide rods 60. The guide rods 60 are affixed to the plate 54 in spaced relationship therefrom, and are parallel to each other and extend in the dimension of arrows 53. Thus the rods 60, received by brackets 59, guide the plate 52, and attached yoke assembly 36, as it is moved in the dimension of arrows 53 by the drive belt 56.

Another important component of the scanning apparatus 10 comprises means for moving the yoke assembly 36 vertically. Again, while a wide variety of means may be provided, the preferred exemplary means is illustrated in FIGS. 3 through 5. This preferred exemplary means comprises the stepper motor 24-2 which has drive sprocket 61 at the end of the drive shaft thereof, which is connected by a drive belt 62 to a sprocket 63 affixed to lead screw 64. As seen most clearly in FIGS. 4 and 5, the lead screw 64 is mounted so that it extends vertically, with the ends thereof received in bearings in bottom mounting plate 65 and top mounting plate 66. The drive belt 62 is of the same type as the drive belt 56 so that rotation of the sprocket 61 is transformed into a precisely corresponding amount of rotation of the lead screw 64.

The lead screw 64 is received by interiorly threaded ball nut 67, which is mounted by flange 68 to the plate 54. The nut 67 transform rotational movement of the lead screw 64 into linear movement of the plate 54 (and thus the attached yoke assembly 36) in the vertical dimension illustrated by arrows 69 in FIGS. 4 and 5. Movement of the plate 54 is guided in the vertical dimension indicated by arrows 69 by a pair of linearly extending guide posts 70 which are also connected between plates 65 and 66, and conventional linear bearings 71 disposed on either side of the plate 54 and receiving the rods 70.

The structure described so far is sufficient to perform rectilinear scans. The scans may be performed either utilizing the heel holding structure 35 (see FIG. 8 in particular), or the forearm holding structure 72 (see FIG. 9). The heel holding structure 35 preferably comprises a generally contoured hollow body structure 73 which has surface manifestations, shown generally by reference numeral 74, formed thereon for precisely holding the heel of the human subject in place so that the os calcis may be scanned. The surface manifestations 74 include a strip of material 74' that has a substantially right angle bend in it to define one portion supporting the bottom of a subject's heel, and another portion the back of the heel. It also includes a lip 74" which supports the ankle.

If the conical structure 73 is formed of a somewhat radio-opaque material, such as fiberglass, radio-transparent windows, such as acrylic windows, 75 are provided at opposite sides thereof for alignment with the source 28 and detector 27, with the surface means 74 adapted to hold the os calcis so that it is between the windows 75. Where CT functions are also desirable, the holder 35 preferably will be made completely of radio-transparent material, such as acrylic. In either case the holder 35 is water-tight, and water is disposed therein, during use, so that it extends upwardly to the level where it at least completely covers the os calcis. The mounting flange 76 at the open top of the body 73 is adapted to abut the top of the housing 33 while the body 73 is received within the opening 34 in the housing top. Suitable fastening means (not shown) pass through openings 76' in flange 76 to affix the holder 35 in place on housing 33, the positioning of openings 76' and like openings in the top of housing 33 cooperating to properly position the body 73 with respect to the yoke 36.

Figure 8:
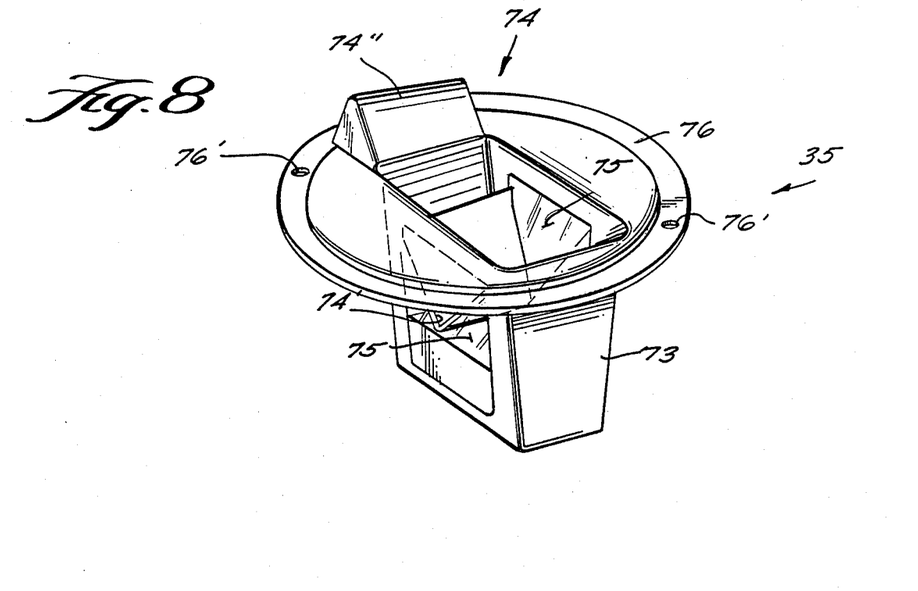
FIG. 8 is a top perspective view of an exemplary heel holding structure utilized with the apparatus of FIG. 1.
Figure 9:
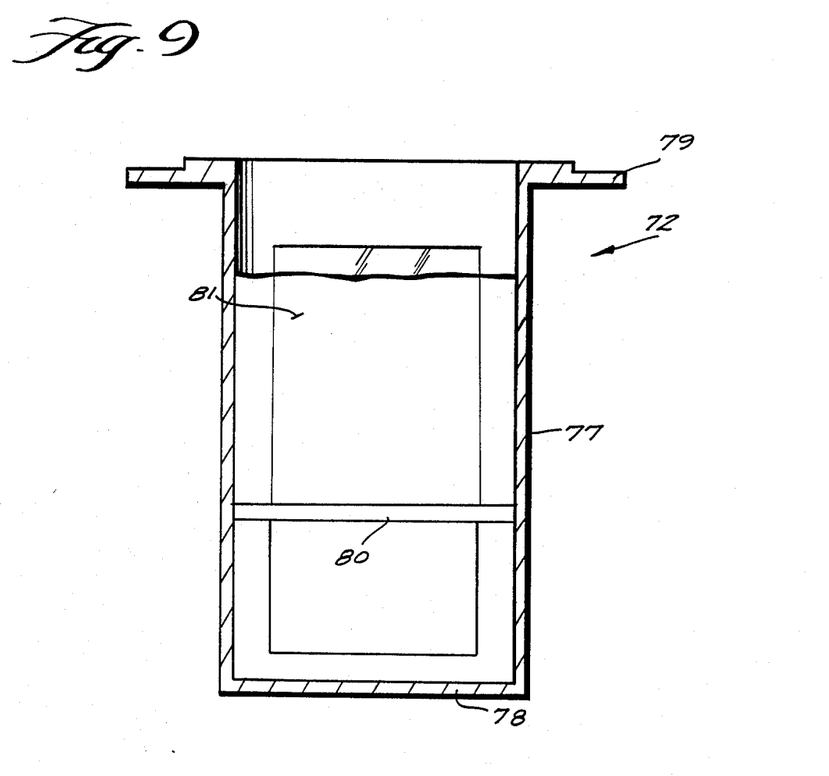
FIG. 9 is a longitudinal cross-sectional view of an exemplary arm holding device that may be utilized in the apparatus of FIG. 1 in place of the heel holding device of FIG. 8.

The arm holding tube 72 illustrated schematically in FIG. 9 may be used in place of the heel holder 35 of FIG. 8. The arm tube 72 comprises a generally rectangular in cross-section tubular body 77 having a closed bottom 78 and an open top with a mounting flange 79 surrounding the open top. The mounting flange 79 is adapted to abut the top of the housing 33 as the tube body 77 extends downwardly into the housing through opening 34 in the housing top, and is held in place just like the flange 76. A hand grip 80 is disposed within the interior of the tube body 77, spanning with width thereof. Grip 80 is grasped by the human subject during use. Unless the tubular body 77 is made of a completely radio-transparent material, a pair of radio-transparent windows 81 (only one of which is shown in FIG. 9) are provided on opposite sides of the body 77 in alignment with the source 28 and detector 27 so that the forearm can be scanned. The window 81 has sufficient dimensions so that both the proximal radius and distal radius may be scanned. The body 77 is also water-tight and water is adapted to be disposed therein during use.

In a typical operation of the structure described so far, when it is desired to make a heel scan the scanner is first calibrated by pressing a function button on keyboard 20 indicating a calibration mode, and with water alone disposed in the heel tube 35. Then the human subject places her heel in the heel tube 35, as illustrated in FIGURE 1, so that the heel is positioned by the surface means 74 and the os calcis can be scanned. The function button on the keyboard 20 is then pressed asking that a heel scan be performed. The software associated with the CPU 12 then initiates actuation of the stepper motor 24-2 and opening of the shutter element 42 so that the yoke assembly 36 moves vertically as the scanner searches for the edge of the os calcis.

Once the edge is located, from this point on the scanner will move up the proper distance for the heel scan. In the performance of a heel scan, at a particular vertical position of the yoke assembly 36 the stepper motor 24-1 is actuated which causes linear movement in dimension 53 of the drive belt 56, and attached yoke assembly 36, with the shutter element 42 in the open position. A typical length of horizontal movement would be 10 centimeters. When that particular length of movement is completed, the shutter element 42 is closed, and the stepper motor 24-1 reverses to drive the yoke assembly 36 in dimension 53 back to its start position. Then, or simultaneously with that movement, the stepper motor 24-2 drives the lead screw 64 to index the yoke assembly 36 one row in the dimension 69. A typical amount of indexing would be three millimeters, the approximate size of the beam from the source 28. This action would be repeated for the number of rows necessary to complete the scanning operation, typically 12 rows in the case of the os calcis.

When the distal radius and proximal radius are scanned, the length of movement of the yoke assembly in dimension 53 is also preferably 10 centimeters in each case, and the spacing of rows is also preferably three millimeters, but in the case of the distal radius there preferably are six rows, and four rows in the case of the proximal radius.

Under some circumstances it may be desirable to perform a CT-type scan in which case it is necessary to also be able to rotate the yoke assembly 36 about a vertical axis. Exemplary means for effecting this rotational movement of the yoke assembly is also illustrated in FIGS. 3 through 5.

A main component of the rotating means comprises the stepper motor 24-3. The shaft of the motor 24-3 terminates in a sprocket 84 (see FIGURES 4 and 5), and extends below the bottom mounting plate 65. The plates 65, 66 mount the entire structure heretofore described, and those plates are in turn mounted by a lazy susan bearing, illustrated at 85 in FIG. 4, to a stationary bottom plate 86 of the scanner 10. The stationary bottom plate 86 has the external housing components 33 of the scanner 10 extending upwardly therefrom, and includes a top portion in which the opening 34 is disposed. Roller bearings 87 extend upwardly from the top plate 66 and engage the top of the housing to assist the lazy susan bearing in mounting all of the components attached to the plates 65, 66 for rotational movement.

The sprocket 84 is connected to the lazy susan bearing 85 by a drive belt 89 (see FIG. 4) which extends around a significant portion of the circumference of the bearing 85. Since there is such good frictional engagement between the drive belt 89 and the external periphery of the bearing 85, it is not necessary to provide sprocket teeth or the like on the bearing 85. Rotation of the sprocket 84 thus results in a precisely related amount of rotation of the bearing 85, and thus the plate 65, yoke assembly 36, and all other structures mounted thereon. In a typical scanning operation utilizing this rotational feature, between each rectilinear scan the yoke assembly 36 could be rotated about 10 degrees.

Figure 10:
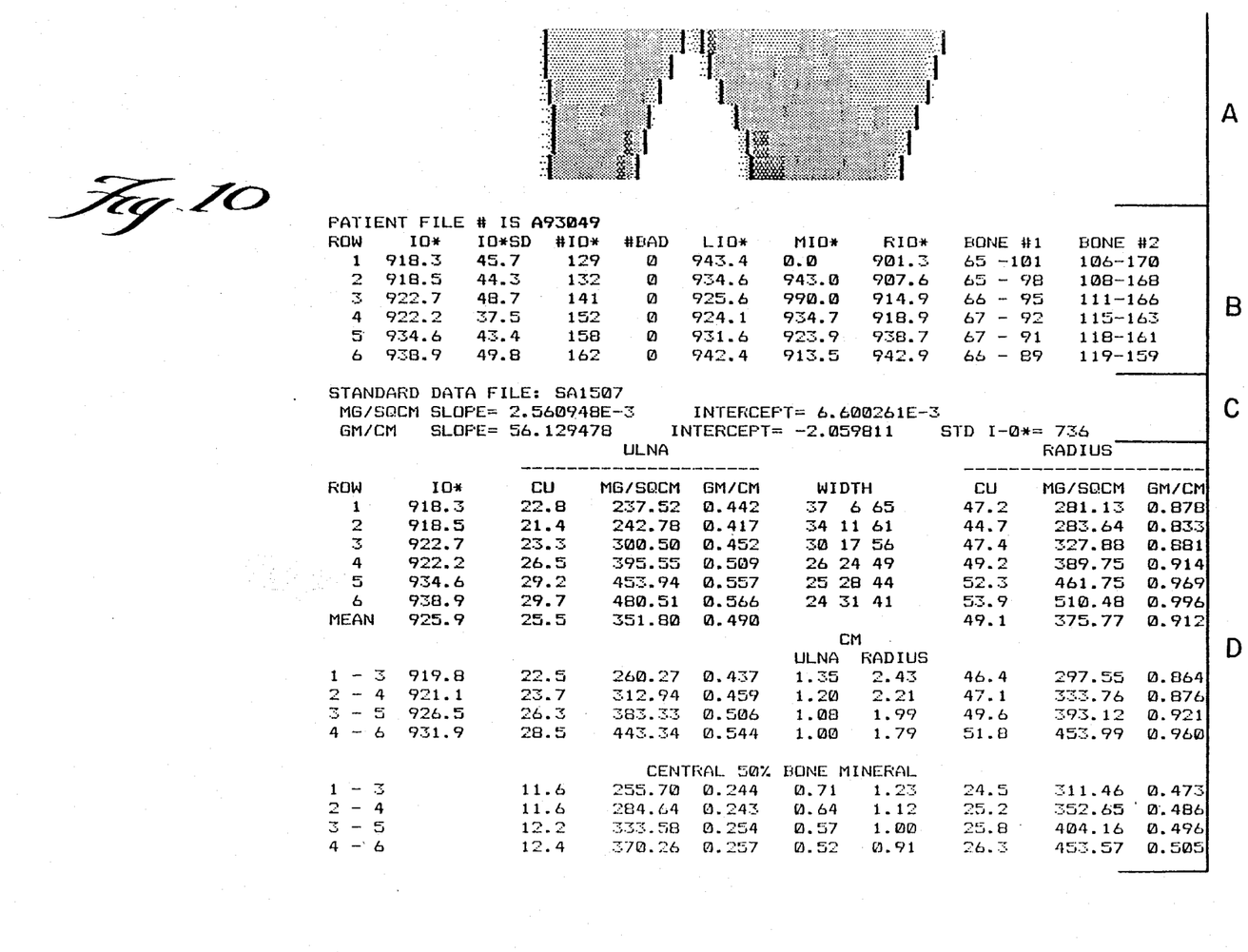
FIG. 10 is an exemplary detailed report for scanning of the distal radius of a subject, which report is obtained by utilizing the apparatus of FIG. 1.

Examples of detailed reports for scans that are accomplished utilizing the present invention are shown in FIGS. 10 through 13. FIG. 10 illustrates an exemplary report for a scan of the distal radius. Before performing a scanner operation utilizing the forearm holder 72, the patient's ulnar length is measured, and that information is inputted into the CPU 12 by the keyboard 20. When the arm scan special function button on the keyboard 20 is pressed, the scanner automatically searches for the proper radial-ulnar split, and when this location has been found the arm scan starts. A proximal radius, as well as distal radius, scan can be selected by properly inputting that command into the computer utilizing the keyboard 20.

In the sample distal radius scan report of FIG. 10, the top section A shows a grey scale based on log $(I_o/I)$ information measured during the scan. The dark lines in each row of the image represent the location of the bone edges as determined by the edge finding alogrithm. In the next section of the report marked B, information on the unattenuated flux $(I_o)$ for each of the rows scanned is given. The column headings shown in the report have the following meanings:

| | |
|---|---|
| ROW | row number from scan |
| IO* | mean unattenuated flux $(I_o*)$ |

| | -continued |
|---|---|
| IO*SD | standard deviation of $I_o^*$ |
| #IO | channels used for $I_o^*$ |
| BAD | calculation number of channel with I outside |
| LIO* | mean I to left of first bone |
| MIO* | mean $I_o^*$ between first and second bone |
| RIO* | mean $I_o^*$ to right second bone |
| BONE #1 | channel number of edges for first bone |
| BONE #2 | channel number of edges for second bone |

The section marked C gives reference information on the calibration values used from the standard calibration. The section D gives detailed information on the total attenuation measured for each row of the scan and the calculated bone mineral for that row. The column headings shown have the following meanings:

| ROW | see above |
|---|---|
| IO* | see above |
| CU | the sum of log $(I_o^*/I)$ for the bone |
| MG/SQCM | bone mineral in mg per square cm |
| GM/CM | bone mineral in gm per cm bone length |
| WIDTH | the channel numbers of left and right edges (outer numbers) and space between bones in channels (center number) |
| CM | width of bone in centimeters |
| CENTRAL 50% | bone mineral as measured over the center 50% of the bone |

Figure 11:
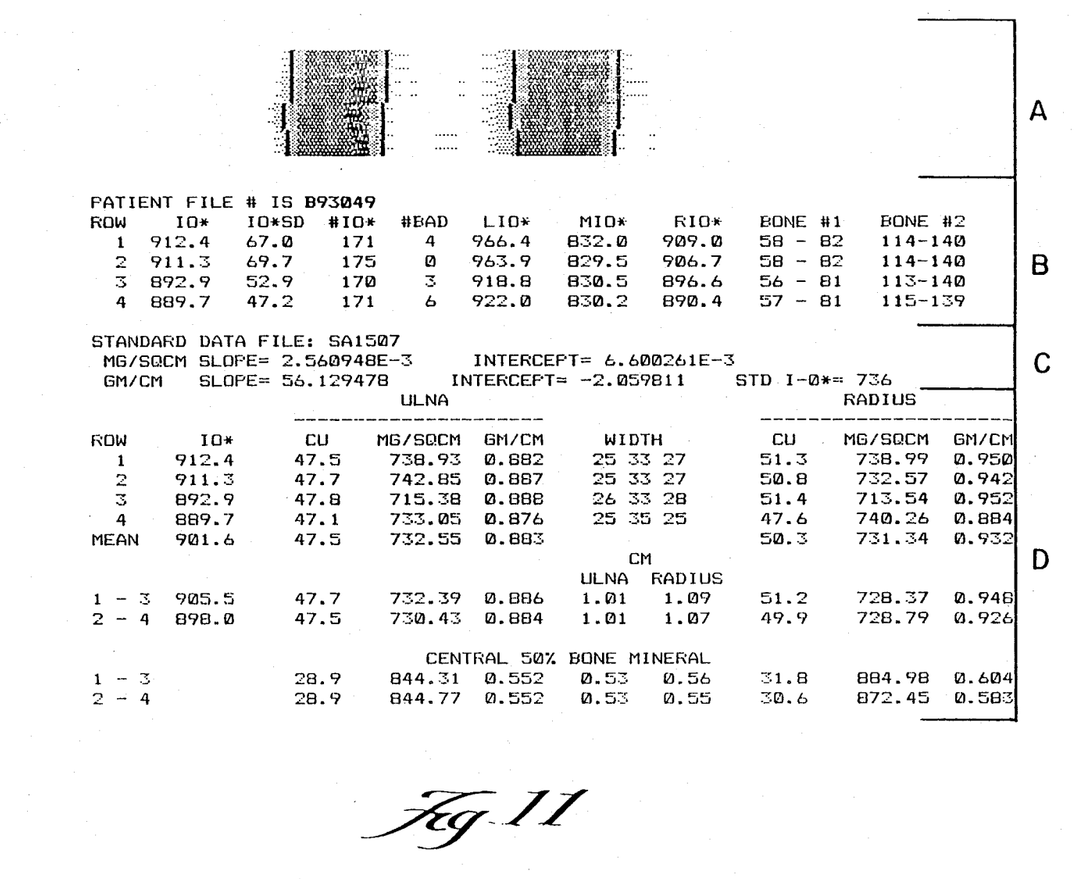
FIG. 11 is an example of a report for the scanning of the proximal radius.

The proximal radius sample report of FIGURE 11 is the same as the report of FIG. 10 except that it is, for course, for the proximal radius instead of the distal radius.

A sample report for the os calcis is given in FIGS. 12a and 12b. FIG. 12a gives information on the standard and unattenuated flux ($I^*_o$) for each of the rows of the scan. The column headings in the first section, marked A, have the following meaning:

| ROW | row number from scan |
|---|---|
| BCH | channel number of first edge |
| ECH | channel number of second edge |
| LEAN SIDE | side of bone with less fat |

The section B of FIG. 12a gives reference information on the calibration values used from the standard calibration file. Section C of FIG. 12a gives information on $I^*_o$, the column headings having the following meanings:

| ROW | row number from scan |
|---|---|
| HIGH | $I_o$ on fatty side of bone |
| LOW | $I_o$ on lean side of bone |
| MEAN | mean $I_o$ |
| CN | number of channels within bone |
| FAT EQU | log ratio of HIGH $I_o^*$ to LOW $I_o^*$ times 6.43 |
| LOW:H2O | ratio of LOW $I_o^*$ to WATER $I_o^*$ |

In FIG. 12b, the section D shows a grey scale based on log ($I^*_o/I$) information measured during the scan. The dark vertical lines in each row represent the location of the bone edges, as determined by the edge finding algorithm. The section marked E gives bone mineral calculations based on three different values for $I^*_o$. The three values for $I^*_o$ are:

| LOW IO | $I_o^*$ from lean side of bone |
|---|---|
| H2O IO | $I_o^*$ from calibration standard |
| MEAN IO | mean $I_o^*$ for row |

The column headings for each $I^*_o$ have the following meanings:

| CU | the sum of log $(I_o^*/I)$ for the bone |
|---|---|
| MG/SQCM | bone mineral in mg per square cm |
| GM/CM | bone mineral in gm per cm bone length |

The section marked F in FIG. 12b gives summary bone mineral information when averaged over a number of rows. The column headings in section F have the following meanings:

| ROW | rows used for calculations |
|---|---|
| CU | the sum of log $(I_o^*/I)$ for rows above |
| MG/SQCM WEDGE | bone mineral content in mg./cm.$^2$ |
| GM/CM | gm per cm bone mineral content |
| AREA SQCM | area of bone scanned in square centimeters |
| BMC GRAMS | total bone mass (MG/SQCM × SQCM) |
| BMD GM/SQCM | bone mineral density (BMC/SQCM). |

Figure 13:
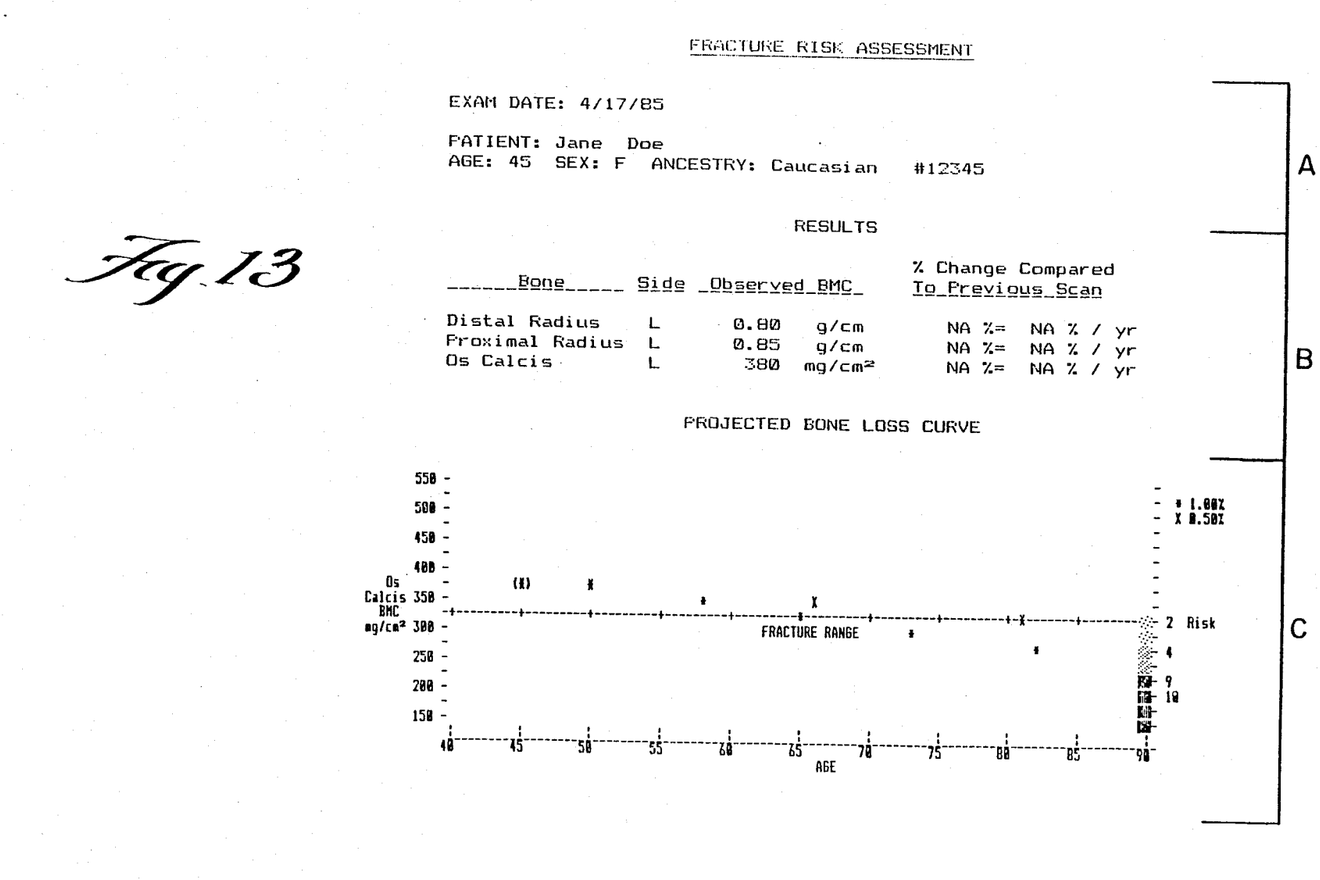
FIG. 13 is an example of a risk assessment report that may be prepared according to the invention.
Figure 16A:
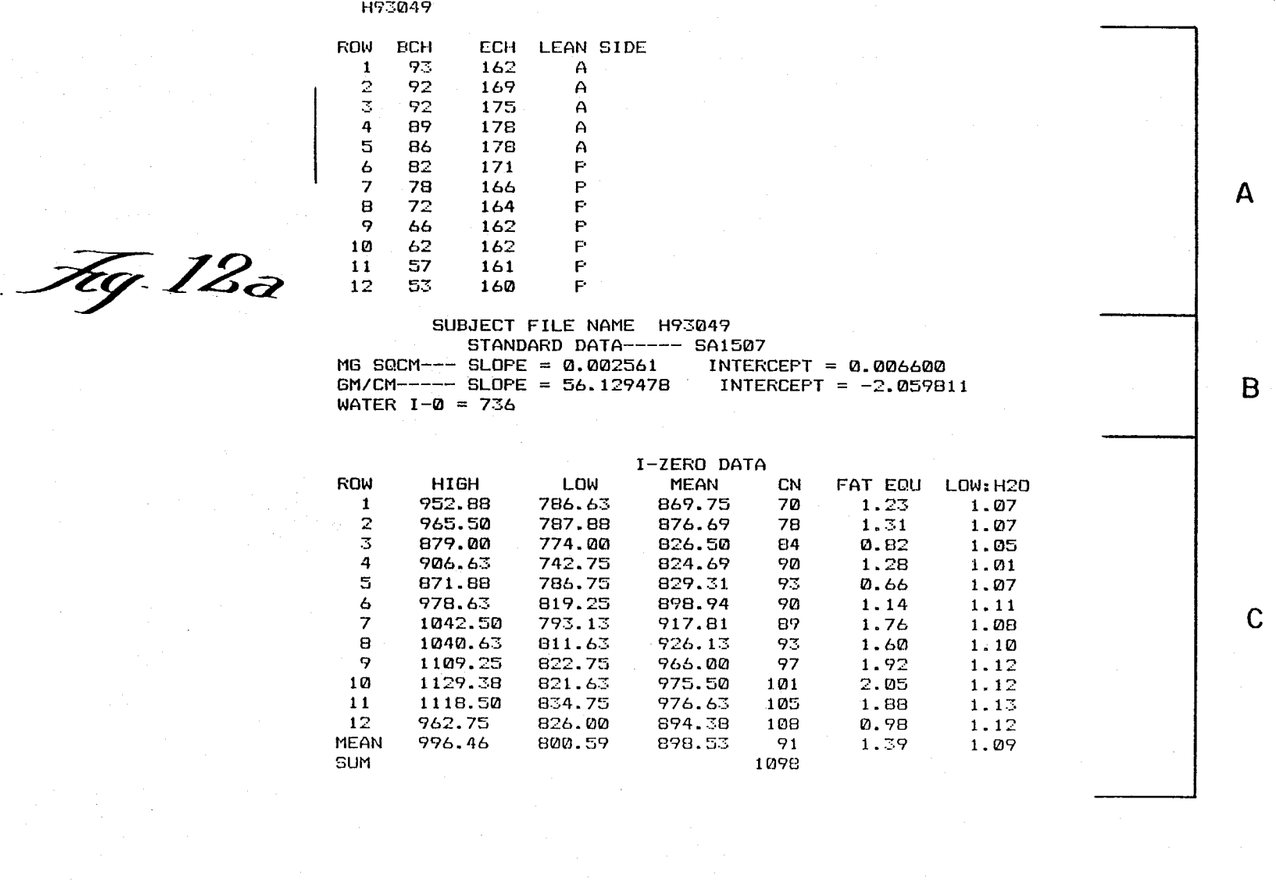
Figure 18B:
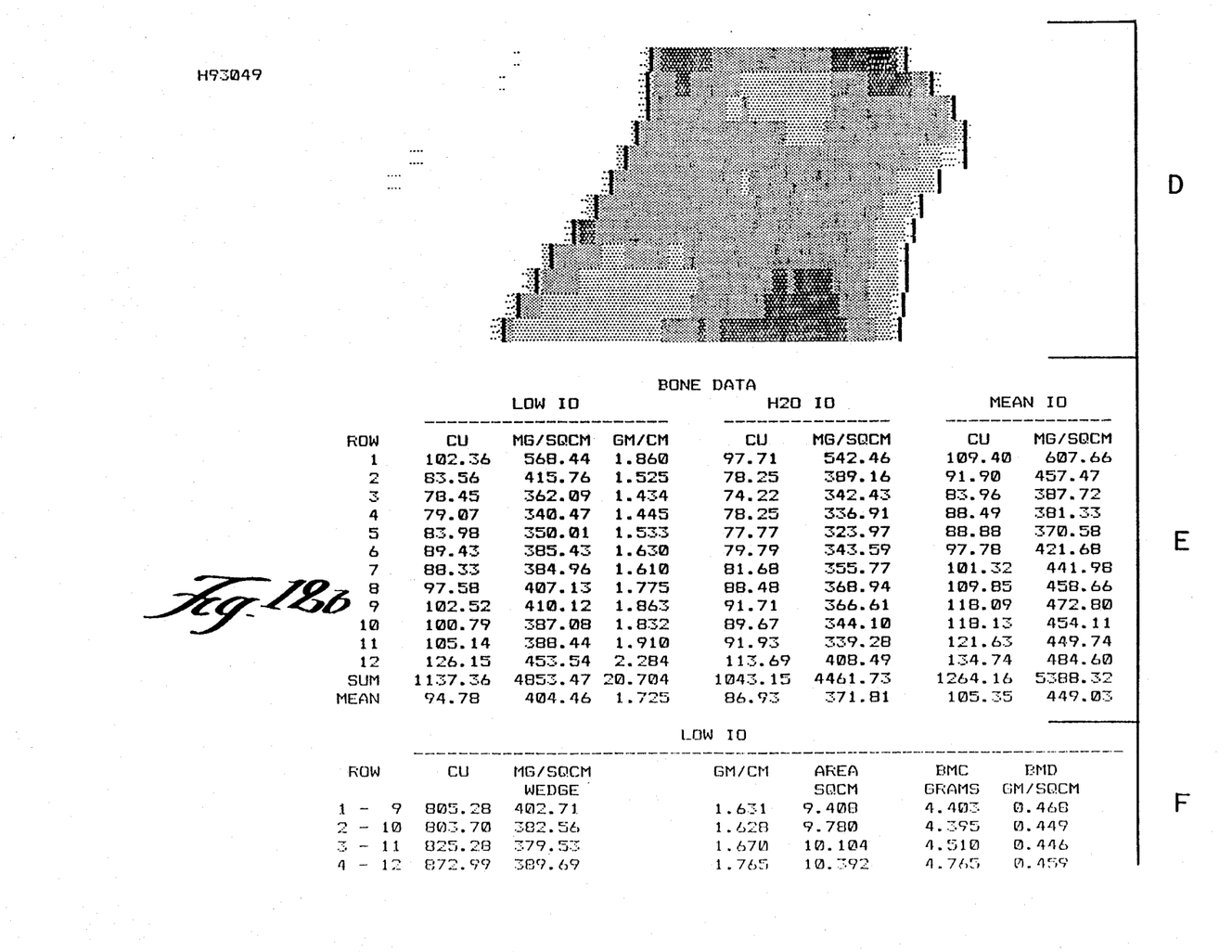

A sample relative risk assessment report is given in FIG. 13. The first section A of that report gives patient history. The second section, B, gives the numerical results of the patient scan. The os calcis measurement in mg/cm$^2$ is always given, as this reading is used for the measurement of fracture risk. The 380 mg/cm$^2$ value in section B of the report represents the lowest bone mineral reading (rounded) of the nine row averages as reported in section F of FIG. 12b. The distal and proximal radius measurements in gm/cm are also given if the measurements were done.

The section C of the report of FIG. 13 gives the fracture risk assessment based on the os calcis measurement made, along with an estimate of fracture risk in future years. The fracture risk line corresponds to the os calcis measurement with a risk factor twice as great as young normals. The estimate of future fracture risk is also shown in section C. The estimated bone mineral for the patient is plotted graphically, based on a loss rate entered by the operator if it is the patient's first scan, or calculated by the computer where there is information in memory from one or more earlier scans of the same patient. The probable risk of fracture in future years can be estimated from the line drawn.

A second loss curve is also plotted for the estimated bone mineral with a lower loss rate entered by the operator (normally one-half the first loss rate). The purpose of the second plot is to show the dramatic delay in crossing the fracture risk line for a very small decrease in loss rate, not to predict the result of any particular therapy.

Utilizing the apparatus 10, 11 according to the present invention it is possible to quickly determine the relative level of risk of osteoporosis in human subjects by determining the bone mineral content of the os calcis, and assessing fracture risk at multiple (substantially all) skeletal sites from the os calcis mineral content determined.

Most accurate fracture prediction can usually be obtained when the human subject's os calcis is first scanned (a base scan) at the human subject's peak bone mass age. For instance a typical perimenopausal women would be scanned at age 35. Subsequently, periodic scans would be made of the subject's os calcis, and the additional scanning information would be acted upon by the computer in preparing the risk assessment report of FIG. 13, as described above. The information is particularly useful when subsequent scans of the human subject are postmenopausal.

Treatment of the human subject can be prescribed depending upon the level of risk prediced and available therapeutic agents. For instance exercise and calcium supplements may be prescribed where the risk is slightly greater than normal. Estrogen, or estrogen thiazide, treatments may also be prescribed, or where indicated sodium fluoride treatments may be utilized. For aggressive treatments the apparatus 10, 11 may be used to also monitor a cortical bone site of the human subject, preferably the distal radius, to make sure that the treatment does not have undue adverse effects on cortical bone.

While the invention has been herein shown and described with respect to determining bone mineral content by scanning utilizing low energy gamma rays and/or x-rays, other known techniques for determining bone mineral content may also be utilized. A key factor is the ability of predict relative fracture risk at substantially all skeletal sites from determinations made only of the os calcis. If after screening utilizing the os calcis, further analysis is also deemed necessary, the patient can be subjected to additional bone mineral content evaluations of other bones (such as the spine) utilizing other known techniques and apparatus aside from those described herein.

The method and apparatus according to the present invention thus results in a simple, accurate, and relatively inexpensive screening program which used in conjunction with adequate therapy can make clinically significant osteoporosis an analomy among the present generation of perimenopausal women, and significantly reduce the incidence of hip fracture among postmenopausal women. When osteopenia is discovered at the stage when women enter their perimenopausal period, preventative measures can be taken to ensure that the rapid acceleration in loss rate seen in the perimenopausal period does not progress to clinically significant osteoporosis. Utilizing the apparatus and techniques according to the invention it is also possible to measure the response to treatment in individuals with established osteoporosis, and to monitor the effectiveness of preventive regimens.

While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent methods and apparatus.

What is claimed is:

1. A method for determining the relative level of risk of osteoporosis in a human subject comprising the steps of:
    (a) providing an os calcis scanning apparatus including a housing with means for holding a heel of the human subject in proper position during scanning; a source of low energy x-ray or gamma radiation; radiation detecting means; a scanning yoke disposed with the housing for mounting said source and said detecting means opposite each other with a volume therebetween sufficient to receive the holding means; means for moving said yoke vertically, horizontally and rotationally about a vertical axis within said housing; and computer control means for controlling movement of said yoke during scanning;
    (b) locating a bottom edge of the os calcis when the heel is properly positioned in the holding means;
    (c) moving the scanning yoke to a vertical and horizontal start position at a first row;
    (d) moving the scanning yoke horizontally to scan the row, with radiation passing between the source and the detector;
    (e) retracting the scanning yoke horizontally to the horizontal start position and indexing the scanning yoke vertically a predetermined distance to a second row;
    (f) repeating steps (d) and (e) until at least twelve rows are scanned;
    (h) determining a nine row average of the said at least twelve rows which gives the lowest bone mineral reading and indicating the risk of fracture of a bone of said subject.

2. A method as defined in claim 1 wherein, in step (d), the scanning yoke is moved horizontally about 10 centimeters.

3. A method as defined in claim 1 wherein, in step (e), the scanning yoke is indexed vertically a distance of about three millimeters for each row.

4. A method as defined in claim 1 and further including the step of rotating the scanning yoke about 10 degrees about a vertical axis during step (e).

* * * * *